United States Patent
Janapaty

(10) Patent No.: US 11,583,904 B2
(45) Date of Patent: Feb. 21, 2023

(54) METHODS FOR DEGRADING LOW DENSITY POLYETHYLENE (LDPE) AND REMEDIATING LEACHATE

(71) Applicant: Shloka Janapaty, San Jose, CA (US)

(72) Inventor: Shloka Janapaty, San Jose, CA (US)

( * ) Notice: Subject to any disclaimer, the term of this patent is extended or adjusted under 35 U.S.C. 154(b) by 332 days.

(21) Appl. No.: 16/849,026

(22) Filed: Apr. 15, 2020

(65) Prior Publication Data
US 2020/0406320 A1  Dec. 31, 2020

Related U.S. Application Data

(60) Provisional application No. 62/834,263, filed on Apr. 15, 2019.

(51) Int. Cl.
*B09B 3/40* (2022.01)
*C08L 23/06* (2006.01)
*C12N 1/14* (2006.01)
*B09B 5/00* (2006.01)

(52) U.S. Cl.
CPC ............... *B09B 3/40* (2022.01); *B09B 5/00* (2013.01); *C08L 23/06* (2013.01); *C12N 1/14* (2013.01); *C08L 2207/066* (2013.01)

(58) Field of Classification Search
CPC .... B09B 3/40; B09B 5/00; C12N 1/14; C08L 23/06; C08L 2207/066
USPC .......................................................... 588/313
See application file for complete search history.

(56) References Cited

PUBLICATIONS

Drummond et al., "Crystallization of low-density polyethylene-and linear low-density polyethylene-rich blends," Journal of applied polymer science, Oct. 31, 2000, 78(5):1009-1016.
Kim et al., "Treatment of landfill leachate by white rot fungus in combination with zeolite filters," Journal of Environmental Science and Health, Part A, May 1, 2003, 38(4): 15 Pages.
Mijovic et al., "Etching of polymeric surfaces: A review. Polymer-Plastics Technology and Engineering," Jan. 1, 1977, 9(2): 43 Pages.

*Primary Examiner* — Edward M Johnson
(74) *Attorney, Agent, or Firm* — Fish & Richardson P.C.

(57) ABSTRACT

This document relates to methods for degrading Low Density Polyethylene (LDPE) and remediating leachate. This document provides methods involved in contacting pre-treated LDPE or plastic waste comprising LDPE with at least one white-rot fungus, achieving near 100% LDPE degradation.

20 Claims, 4 Drawing Sheets

Day 0

Day 6

Day 3

Day 6

METHODS FOR DEGRADING LOW DENSITY POLYETHYLENE (LDPE) AND REMEDIATING LEACHATE

CROSS-REFERENCE TO RELATED APPLICATIONS

This application claims priority to U.S. Provisional Application Ser. No. 62/834,263, filed on Apr. 15, 2019, the contents of which are hereby incorporated by reference in their entirety.

BACKGROUND

1. Technical Field

This document relates to methods for degrading Low Density Polyethylene (LDPE) and remediating leachate. For example, this document relates to methods involved in contacting pretreated LDPE or plastic waste comprising LDPE with at least one white-rot fungus, achieving near 100% LDPE degradation.

2. Background Information

LDPE is a thermoplastic made from the monomer ethylene that is widely used for manufacturing various containers, dispensing bottles, wash bottles, tubing, and plastic bags. Although a small portion of the plastic waste is disposed of by combustion, most of the waste is buried in landfills. Burning plastic waste is expensive and releases toxic gases, including dioxins and furans. Most plastic waste ends up in landfill sites, which leads to serious environmental problems. For example, plastic pollution makes up about 40 percent of ocean surface, affecting at least 700 marine species. It is estimated that at least 100 million marine mammals are killed each year from plastic pollution. As one of the highly non-biodegradable plastic, LDPE makes up a substantial portion of the world's plastic waste. LDPE in landfills takes over 500 years to decompose. Additionally, landfill leachate (e.g., activated sludge) is a major threat to water bodies and human health even at trace levels. In most temperate and tropical climates, landfills will unavoidably produce leachate. Current treatment methods for leachate are expensive and inefficient. There is a need for developing efficient methods for leachate remediation in landfills.

SUMMARY

This document provides methods for degrading Low Density Polyethylene (LDPE) and remediating leachate.

The methods disclosed herein can be used on-site, at landfills, at a low cost. The methods disclosed herein can be implemented feasibly using the activated sludge infrastructure of existing landfills. The methods disclosed herein can mitigate the dumping of LDPE into oceans, as LDPE can be degraded nearly 100% in 6 days, without producing toxic byproducts. Furthermore, the methods disclosed herein can also remediate leachate and improve the environment for human health.

Other features and advantages of the invention will be apparent from the following detailed description, and from the claims.

DESCRIPTION OF THE DRAWINGS

FIG. 5A: control; FIG. 5B: synthetic leachate+*Phanerochaete chrysosporium*, at Day 0; FIG. 5C: synthetic leachate+*Phanerochaete chrysosporium*+LDPE, at Day 12.

DETAILED DESCRIPTION

Figure 1:
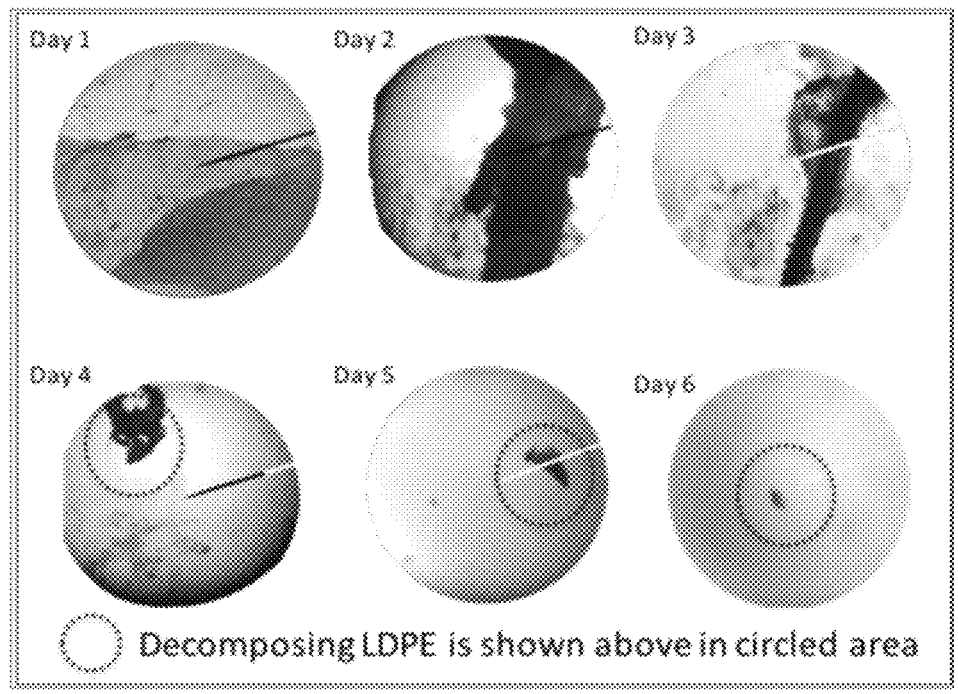
FIG. 1: Microscopic images for Group 8 that achieved near 100% LDPE decomposition.

This document provides methods for degrading Low Density Polyethylene (LDPE) and remediating leachate. For example, this document relates to methods of contacting pretreated LDPE or plastic waste comprising LDPE with at least one white-rot fungus (e.g., a composition comprising at least one white-rot fungus). In some embodiments, the methods provided herein result in a near 100% LDPE degradation.

This document further provides methods for degrading LDPE comprising heating LDPE at a temperature of about 90° C. to about 150° C. and contacting the LDPE with at least one white-rot fungus (e.g., a composition comprising at least one white-rot fungus). Also provided herein are methods for degrading LDPE comprising heating plastic waste comprising LDPE at a temperature of about 90° C. to about 150° C. and contacting the plastic waste with at least one white-rot fungus (e.g., a composition comprising at least one white-rot fungus). Also provided herein are methods for degrading LDPE comprising etching LDPE and contacting the LDPE with at least one white-rot fungus (e.g., a composition comprising at least one white-rot fungus). This document further provides a method for degrading LDPE comprising etching plastic waste comprising LDPE and contacting the plastic waste with at least one white-rot fungus (e.g., a composition comprising at least one white-rot fungus). This document further provides a method for degrading LDPE comprising heating LDPE, etching the LDPE, and contacting the LDPE with at least one white-rot fungus (e.g., a composition comprising at least one white-rot fungus). This document further provides a method for degrading LDPE comprising heating plastic waste comprising LDPE, etching the plastic waste, and contacting the plastic waste comprising LDPE with at least one white-rot fungus (e.g., a composition comprising at least one white-rot fungus).

In some embodiments, the at least one white-rot fungus may be selected from a group consisting of *Phanerochaete* fungus, *Phlebia* fungus, *Trametes* fungus, *Pleurotus* fungus, *Bjerkandera* fungus, and mixtures thereof. In some embodiments, the at least one white-rot fungus may be selected from a group consisting of *Phanerochaete chrysosporium, Phanerochaete sordida, Pleurotus ostreatus, Pleurotus ostreatus* var. *columbinus, Lentinula edodes, Ganoderma lucidum, rametes versicolor, Bjerkandera adjusta, Trametes versicolor, Pleurotus ostreatus,* and mixtures thereof. In some embodiments, the at least one white-rot fungus is a

*Phanerochaete* fungus. In some cases, the *Phanerochaete* fungus may be selected from a group consisting of *Phanerochaete aculeata, Phanerochaete affinis, Phanerochaete alba, Phanerochaete albida, Phanerochaete allantospora, Phanerochaete alnea, Phanerochaete aluticolor, Phanerochaete andreae, Phanerochaete angustocystidiata, Phanerochaete arenata, Phanerochaete areolata, Phanerochaete argillacea, Phanerochaete arizonica, Phanerochaete aurantiobadia, Phanerochaete australis, Phanerochaete avellanea, Phanerochaete bambucicola, Phanerochaete binucleospordida, Phanerochaete brunnea, Phanerochaete bubalina, Phanerochaete burtii, Phanerochaete cacaina, Phanerochaete cana, Phanerochaete capitata, Phanerochaete carnosa, Phanerochaete caucasica, Phanerochaete citri, Phanerochaete citrinosanguinea, Phanerochaete commixtoides, Phanerochaete conifericola, Phanerochaete cordylines, Phanerochaete cremeo-ochracea, Phanerochaete crescentispora, Phanerochaete cryptocystidiata, Phanerochaete deflectens, Phanerochaete eburnea, Phanerochaete eichleriana, Phanerochaete emplastra, Phanerochaete exigua, Phanerochaete exilis, Phanerochaete flava, Phanerochaete flavidogrisea, Phanerochaete flavocarnea, Phanerochaete fulva, Phanerochaete furfuraceovelutinus, Phanerochaete globosa, Phanerochaete granulata, Phanerochaete hiulca, Phanerochaete hyphocystidiata, Phanerochaete incarnata, Phanerochaete incrustans, Phanerochaete infuscata, Phanerochaete intertexta, Phanerochaete investiens, Phanerochaete jose-ferreirae, Phanerochaete laevis, Phanerochaete leptoderma, Phanerochaete lutea, Phanerochaete luteoaurantiaca, Phanerochaete macrocystidiata, Phanerochaete martelliana, Phanerochaete mauiensis, Phanerochaete odontoidea, Phanerochaete oreophila, Phanerochaete pallida, Phanerochaete parmastoi, Phanerochaete parvispora, Phanerochaete percitrina, Phanerochaete phosphorescens, Phanerochaete porostereoides, Phanerochaete pseudosanguinea, Phanerochaete queletii, Phanerochaete radulans, Phanerochaete reflexa, Phanerochaete rhodella, Phanerochaete robusta, Phanerochaete rubescens, Phanerochaete sacchari, Phanerochaete salmoneolutea, Phanerochaete sanguineocarnosa, Phanerochaete sanwicensis, Phanerochaete sordida, Phanerochaete stereoides, Phanerochaete suballantoidea, Phanerochaete subceracea, Phanerochaete subcrassispora, Phanerochaete subglobosa, Phanerochaete subiculosa, Phanerochaete taiwaniana, Phanerochaete tamariciphila, Phanerochaete thailandica, Phanerochaete tropica, Phanerochaete tuberculascens, Phanerochaete tuberculata, Phanerochaete velutina, Phanerochaete vesiculosa, Phanerochaete xerophila*, and mixtures thereof. In some embodiments, the at least one white-rot fungus comprises *Phanerochaete chrysosporium*. In some embodiments, the at least one white-rot fungus is *Phanerochaete chrysosporium*.

In some cases, the at least one white-rot fungus produces manganese peroxidase. In some cases, the at least one white-rot fungus produces lignin peroxidase. In some cases, the at least one white-rot fungus produces manganese peroxidase and lignin peroxidase.

In some embodiments, the at least one white-rot fungus is not present on the LDPE prior to the contacting. In some embodiments, the at least one white-rot fungus is not native to the plastic waste comprising the LDPE prior to the contacting. For example, the at least one white-rot fungus is exogenous to the plastic waste comprising LDPE (e.g., the landfill comprising the LDPE) prior to the contacting. In some embodiments, the at least one white-rot fungus is not naturally present in the plastic waste comprising the LDPE prior to the contacting.

As used herein "contacting" can include any method of introducing the at least one white-rot fungus onto or into the LDPE or the plastic waste comprising LDPE. For example, inoculating the LDPE or the plastic waste comprising LDPE with the at least one white-rot fungus (e.g., a composition comprising at least one white-rot fungus), immersing the LDPE or the plastic waste comprising LDPE into a composition comprising the at least one white-rot fungus, adding the at least one white-rot fungus (e.g., a composition comprising a white-rot fungus) to the LDPE or the plastic waste comprising LDPE (e.g., by spray, by shovel, by large surface moving machine (e.g., a backhoe). In some embodiments, the at least one white-rot fungus is inoculated at an optical density of 2.5 in a 10 µL inoculation solution.

In some embodiments, the LDPE or the plastic waste comprising LDPE is contacted with an amount of at least one white-rot fungus to colonize the LDPE with the at least one white-rot fungus.

LDPE consists of long chain molecules, with —$CH_2CH_2$— repeating units. This structure interferes with crystallization. When LDPE is heated, crystallization occurs, weakening the chemical bonds in LDPE (Drummond, K. M. et al., *Journal of Applied Polymer Science*, 2000, 78:5, 1009-16). The LDPE surface can also converted from hydrophobic to hydrophilic following heating, giving rise to more sites for the fungus to anchor, for example, due to the anchorage dependency of the white-rot fungus (e.g., *Phanerochaete chrysosporium*). In some cases, LDPE may be heated at a temperature of about 90° C. to about 150° C. For example, the LDPE may be heated at a temperature of about 110° C. to about 130° C. In some cases, LDPE may be heated at a temperature of about 120° C. In some cases, LDPE may be heated for about 2 minutes to about 10 minutes (e.g., about 2 minutes to about 5 minutes, about 2 minutes to about 4 minutes, about 2 minutes to about 8 minutes, about 3 minutes to about 6 minutes, about 4 minutes to about 7 minutes, about 5 minutes to about 10 minutes, about 6 minutes to about 9 minutes, or about 8 minutes to about 10 minutes). In some embodiments, the LDPE is heated for at least about 2 minutes. In some cases, LDPE is heated for at least about 4 minutes. In some cases, LDPE may be heated for 4 minutes.

In some cases, plastic waste comprising LDPE may be heated at a temperature of about 90° C. to about 150° C. In some cases, plastic waste comprising LDPE may be heated at a temperature of about 110° C. to about 130° C. In some cases, plastic waste comprising LDPE may be heated for about 2 minutes to about 10 minutes (e.g., about 2 minutes to about 5 minutes, about 2 minutes to about 4 minutes, about 2 minutes to about 8 minutes, about 3 minutes to about 6 minutes, about 4 minutes to about 7 minutes, about 5 minutes to about 10 minutes, about 6 minutes to about 9 minutes, or about 8 minutes to about 10 minutes). In some embodiments, the plastic waste comprising LDP is heated for at least about 2 minutes. In some cases, plastic waste comprising LDP is heated for at least about 4 minutes. In some cases, LDPE may be heated for 4 minutes.

Any suitable method can be used for heading the LDPE or the plastic waste comprising LDPE. For example, in some embodiments, the LDPE or the plastic waste comprising LDPE will be heated by landfill heat (e.g., the heat generated from degradation of various waste types as a result of chemical and biological processes). In some embodiments, the LDPE or the plastic waste comprising LDPE can be heated in ovens or through the application of external heat. For example, radiant heaters, convection heaters, fan heaters, and immersion heaters can be used. In some embodiments, other industrial methods of heating materials such as steam based heating systems, fuel based process heating systems, electric process heating systems, and hybrid process heating systems can be used.

Etching treatment can be used to change the morphology of polymers and increase the surface area of polymers (Mijovic, J. S., *Polymer-Plastics Technology and Engineering*, 2006, 9:2, 139-179). This process can give rise to a larger density of sites for the subsequent metal deposition or more sites for fungi to anchor. In many cases, the chemical reactivity of etched surfaces also increases upon etching. By etching, some polymeric surfaces can be converted from hydrophobic to hydrophilic (Mijovic, J. S., *Polymer-Plastics Technology and Engineering*, 2006, 9:2, 139-179).

Any suitable etching method may be used for etching LDPE or plastic comprising LDPE. Examples include but not limited to chemical etching (e.g., chromic acid), physical etching (e.g., abrasion), and ultrasound etching. In some cases, a weak organic acid may be used for etching. The term "weak acid" as used herein is intended to mean any acid with a pKa of at least 3. In some cases, the weak organic acid is selected from a group consisting of lactic acid, citric acid, malic acid, oxalic acid, acetic acid, tartaric acid, adipic acid, succinic acid, maleic acid, glutamic acid, fumaric acid, pyruvic acid, gluconic acid, picric acid, aspartic acid, terebic acid, and mixtures thereof. In some embodiments, the acid is citric acid. For example, the acid may be 3% citric acid. In some embodiments, the LDPE is etched for about 5 minutes to about 20 minutes (e.g., about 5 minutes to about 10 minutes, about 5 minutes to about 7 minutes, about 7 minutes to about 12 minutes, about 8 minutes to about 10 minutes, about 8 minutes to about 12 minutes, about 10 minutes to about 20 minutes, about 10 minutes to about 15 minutes, about 15 minutes to about 20 minutes, and about 14 minutes to about 18 minutes). In some cases, the LDPE may be etched for at least about 8 minutes. In some embodiments, the LDPE is etched for at least about 10 minutes. In some cases, LDPE may be etched for about 10 minutes. In some cases, at least one hydrophobic portion of the LDPE is converted to hydrophilic after etching.

Despite being a problem in landfills, the leachate (e.g., activated sludge) can play a role in improving LDPE degradation in the methods provided herein. The high carbon/nitrogen ratio in leachate can, for example, enhance *Phanerochaete* fungus growth and stimulate the release of enzymes (Kim, Y. K. et al., *J Environ Sci Health A Tox Hazard Subst Environ Eng.*, 2003 April; 38(4): 671-83). These enzymes, such as manganese peroxidase, are a secondary metabolic response of *Phanerochaete* fungus. The enzymes aid the degradation of LDPE. In some cases, the enzymes can further act to remediate the leachate, making it safe for disposal. In some cases, a high-carbon/nitrogen (C/N)-ratio medium may be added to the LDPE or the plastic waste comprising LDPE. In some cases, the C/N ratio is of at least 20. In some cases, the C/N ratio is of at least 35. In some cases, the medium may comprise leachate. In some cases, the leachate may be synthetic leachate. In some cases, the pH of the medium is at about pH 3.5 to about pH 5. In some cases, the pH of the medium is at about pH 4.0 to about pH 4.5. In some cases, the pH of the plastic waste or the LDPE is at about pH 2.5 to about pH 6.

In some cases, the temperature of the plastic waste or the LDPE after heating is maintained at about 25° C. to about 60° C.

In some embodiments, the methods provided herein further comprise adding agar, compost, organic waste, wood waste, woodchips or sawdust to the plastic waste or the LDPE. In some cases, woodchips or sawdust are added to the plastic waste or the LDPE. In some cases, the medium is pinewood sawdust.

In some cases, at least 50% of the LDPE by weight is degraded in twelve days following contacting the LPDE or plastic waste comprising LPDE with the at least one white-rot fungus. In some cases, at least 60% of the LDPE by weight is degraded in twelve days following contacting the LPDE or plastic waste comprising LPDE with the at least one white-rot fungus. In some cases, at least 70% of the LDPE by weight is degraded in twelve days following contacting the LPDE or plastic waste comprising LPDE with the at least one white-rot fungus. In some cases, at least 80% of the LDPE by weight is degraded in twelve days following contacting the LPDE or plastic waste comprising LPDE with the at least one white-rot fungus. In some cases, at least 90% of the LDPE by weight is degraded in twelve days following contacting the LPDE or plastic waste comprising LPDE with the at least one white-rot fungus. In some cases, at least 95% of the LDPE by weight is degraded in twelve days following contacting the LPDE or plastic waste comprising LPDE with the at least one white-rot fungus. In some cases, at least 99% of the LDPE by weight is degraded in twelve days following contacting the LPDE or plastic waste comprising LPDE with the at least one white-rot fungus. In some cases, at least 99.5% of the LDPE by weight is degraded in twelve days following contacting the LPDE or plastic waste comprising LPDE with the at least one white-rot fungus. In some cases, at least 99.9% of the LDPE by weight is degraded in twelve days following contacting the LPDE or plastic waste comprising LPDE with the at least one white-rot fungus.

In some cases, at least 50% of the LDPE by weight is degraded in six days following contacting the LPDE or plastic waste comprising LPDE with the at least one white-rot fungus. In some cases, at least 60% of the LDPE by weight is degraded in six days following contacting the LPDE or plastic waste comprising LPDE with the at least one white-rot fungus. In some cases, at least 70% of the LDPE by weight is degraded in six days following contacting the LPDE or plastic waste comprising LPDE with the at least one white-rot fungus. In some cases, at least 80% of the LDPE by weight is degraded in six days following contacting the LPDE or plastic waste comprising LPDE with the at least one white-rot fungus. In some cases, at least 90% of the LDPE by weight is degraded in six days following contacting the LPDE or plastic waste comprising LPDE with the at least one white-rot fungus. In some cases, at least 95% of the LDPE by weight is degraded in six days following contacting the LPDE or plastic waste comprising LPDE with the at least one white-rot fungus. In some cases, at least 99% of the LDPE by weight is degraded in six days following contacting the LPDE or plastic waste comprising LPDE with the at least one white-rot fungus. In some cases, at least 99.5% of the LDPE by weight is degraded in six days following contacting the LPDE or plastic waste comprising LPDE with the at least one white-rot fungus. In some cases, at least 99.9% of the LDPE by weight is degraded in six days following contacting the LPDE or plastic waste comprising LPDE with the at least one white-rot fungus.

In some cases, at least 50% of the LDPE surface area is degraded in twelve days following contacting the LPDE or plastic waste comprising LPDE with the at least one white-rot fungus. In some cases, at least 60% of the LDPE surface area is degraded in twelve days following contacting the LPDE or plastic waste comprising LPDE with the at least one white-rot fungus. In some cases, at least 70% of the LDPE surface area is degraded in twelve days following contacting the LPDE or plastic waste comprising LPDE with the at least one white-rot fungus. In some cases, at least 80% of the LDPE surface area is degraded in twelve days following contacting the LPDE or plastic waste comprising LPDE with the at least one white-rot fungus. In some cases, at least 90% of the LDPE surface area is degraded in twelve days following contacting the LPDE or plastic waste comprising LPDE with the at least one white-rot fungus. In some cases, at least 95% of the LDPE surface area is degraded in twelve days following contacting the LPDE or plastic waste comprising LPDE with the at least one white-rot fungus. In some cases, at least 99% of the LDPE surface area is degraded in twelve days following contacting the LPDE or plastic waste comprising LPDE with the at least one white-rot fungus. In some cases, at least 99.5% of the LDPE surface area is degraded in twelve days following contacting the LPDE or plastic waste comprising LPDE with the at least one white-rot fungus. In some cases, at least 99.9% of the LDPE surface area is degraded in twelve days following contacting the LPDE or plastic waste comprising LPDE with the at least one white-rot fungus.

In some cases, at least 50% of the LDPE surface area is degraded in six days following contacting the LPDE or plastic waste comprising LPDE with the at least one white-rot fungus. In some cases, at least 60% of the LDPE surface area is degraded in six days following contacting the LPDE or plastic waste comprising LPDE with the at least one white-rot fungus. In some cases, at least 70% of the LDPE surface area is degraded in six days following contacting the LPDE or plastic waste comprising LPDE with the at least one white-rot fungus. In some cases, at least 80% of the LDPE surface area is degraded in six days following contacting the LPDE or plastic waste comprising LPDE with the at least one white-rot fungus. In some cases, at least 90% of the LDPE surface area is degraded in six days following contacting the LPDE or plastic waste comprising LPDE with the at least one white-rot fungus. In some cases, at least 95% of the LDPE surface area is degraded in six days following contacting the LPDE or plastic waste comprising LPDE with the at least one white-rot fungus. In some cases, at least 99% of the LDPE surface area is degraded in six days following contacting the LPDE or plastic waste comprising LPDE with the at least one white-rot fungus. In some cases, at least 99.5% of the LDPE surface area is degraded in six days following contacting the LPDE or plastic waste comprising LPDE with the at least one white-rot fungus. In some cases, at least 99.9% of the LDPE surface area is degraded in six days following contacting the LPDE or plastic waste comprising LPDE with the at least one white-rot fungus.

In some cases, the optical density of the leachate decreases at least 50%. In some cases, the optical density of the leachate decreases at least 60%. In some cases, the optical density of the leachate decreases at least 70%. In some cases, the optical density of the leachate decreases at least 80%. In some cases, the optical density of the leachate decreases at least 90%. In some cases, the optical density of the leachate decreases at least 95%.

In some cases, the optical density of the leachate decreases at least 50% in twelve days following contacting the LPDE or plastic waste comprising LPDE with the at least one white-rot fungus. In some cases, the optical density of the leachate decreases at least 60% in twelve days following contacting the LPDE or plastic waste comprising LPDE with the at least one white-rot fungus. In some cases, the optical density of the leachate decreases at least 70% in twelve days following contacting the LPDE or plastic waste comprising LPDE with the at least one white-rot fungus. In some cases, the optical density of the leachate decreases at least 80% in twelve days following contacting the LPDE or plastic waste comprising LPDE with the at least one white-rot fungus. In some cases, the optical density of the leachate decreases at least 90% in twelve days following contacting the LPDE or plastic waste comprising LPDE with the at least one white-rot fungus. In some cases, the optical density of the leachate decreases at least 95% in twelve days following contacting the LPDE or plastic waste comprising LPDE with the at least one white-rot fungus.

In some cases, the optical density of the leachate decreases at least 50% in six days following contacting the LPDE or plastic waste comprising LPDE with the at least one white-rot fungus. In some cases, the optical density of the leachate decreases at least 60% in six days following contacting the LPDE or plastic waste comprising LPDE with the at least one white-rot fungus. In some cases, the optical density of the leachate decreases at least 70% in six days following contacting the LPDE or plastic waste comprising LPDE with the at least one white-rot fungus. In some cases, the optical density of the leachate decreases at least 80% in six days following contacting the LPDE or plastic waste comprising LPDE with the at least one white-rot fungus. In some cases, the optical density of the leachate decreases at least 90% in six days following contacting the LPDE or plastic waste comprising LPDE with the at least one white-rot fungus. In some cases, the optical density of the leachate decreases at least 95% in six days following contacting the LPDE or plastic waste comprising LPDE with the at least one white-rot fungus.

In some cases, the concentration of ammonia in the leachate decreases. In some cases, the concentration of ammonia in the leachate decreases to about 0 to about 5.0 ppm. In some cases, the concentration of ammonia in the leachate decreases to about 0 to about 4.0 ppm. In some cases, the concentration of ammonia in the leachate decreases to about 0 to about 3.0 ppm. In some cases, the concentration of ammonia in the leachate decreases to about 0 to about 2.0 ppm. In some cases, the concentration of ammonia in the leachate decreases to about 0 to about 1.0 ppm. In some cases, the concentration of ammonia in the leachate decreases to about 0 to about 0.5 ppm.

In some cases, the concentration of ammonia in the leachate decreases in twelve days following contacting the LPDE or plastic waste comprising LPDE with the at least one white-rot fungus. In some cases, the concentration of ammonia in the leachate decreases to about 0 to about 5.0 ppm in twelve days following contacting the LPDE or plastic waste comprising LPDE with the at least one white-rot fungus. In some cases, the concentration of ammonia in the leachate decreases to about 0 to about 4.0 ppm in twelve days following contacting the LPDE or plastic waste comprising LPDE with the at least one white-rot fungus. In some cases, the concentration of ammonia in the leachate decreases to about 0 to about 3.0 ppm in twelve days following contacting the LPDE or plastic waste comprising LPDE with the at least one white-rot fungus. In some cases, the concentration of ammonia in the leachate decreases to about 0 to about 2.0 ppm in twelve days following contacting the LPDE or plastic waste comprising LPDE with the at least one white-rot fungus. In some cases, the concentration of ammonia in the leachate decreases to about 0 to about 1.0 ppm in twelve days following contacting the LPDE or plastic waste comprising LPDE with the at least one white-rot fungus. In some cases, the concentration of ammonia in the leachate decreases to about 0 to about 0.5 ppm in twelve days following contacting the LPDE or plastic waste comprising LPDE with the at least one white-rot fungus.

In some cases, the concentration of ammonia in the leachate decreases in six days following contacting the LPDE or plastic waste comprising LPDE with the at least one white-rot fungus. In some cases, the concentration of ammonia in the leachate decreases to about 0 to about 5.0 ppm in six days following contacting the LPDE or plastic waste comprising LPDE with the at least one white-rot fungus. In some cases, the concentration of ammonia in the leachate decreases to about 0 to about 4.0 ppm in six days following contacting the LPDE or plastic waste comprising LPDE with the at least one white-rot fungus. In some cases, the concentration of ammonia in the leachate decreases to about 0 to about 3.0 ppm in six days following contacting the LPDE or plastic waste comprising LPDE with the at least one white-rot fungus. In some cases, the concentration of ammonia in the leachate decreases to about 0 to about 2.0 ppm in six days following contacting the LPDE or plastic waste comprising LPDE with the at least one white-rot fungus. In some cases, the concentration of ammonia in the leachate decreases to about 0 to about 1.0 ppm in six days following contacting the LPDE or plastic waste comprising LPDE with the at least one white-rot fungus. In some cases, the concentration of ammonia in the leachate decreases to about 0 to about 0.5 ppm in six days following contacting the LPDE or plastic waste comprising LPDE with the at least one white-rot fungus.

In some cases, the concentration of nitrates in the leachate increases. In some cases, the concentration of nitrates in the leachate increases to at least about 0.5 ppm. In some cases, the concentration of nitrates in the leachate increases to at least about 1 ppm. In some cases, the concentration of nitrates in the leachate increases to at least about 2 ppm. In some cases, the concentration of nitrates in the leachate increases to at least about 3 ppm. In some cases, the concentration of nitrates in the leachate increases to at least about 4 ppm. In some cases, the concentration of nitrates in the leachate increases to at least about 5 ppm.

In some cases, the concentration of nitrates in the leachate increases in twelve days following contacting the LPDE or plastic waste comprising LPDE with the at least one white-rot fungus. In some cases, the concentration of nitrates in the leachate increases to at least about 0.5 ppm in twelve days following contacting the LPDE or plastic waste comprising LPDE with the at least one white-rot fungus. In some cases, the concentration of nitrates in the leachate increases to at least about 1 ppm in twelve days following contacting the LPDE or plastic waste comprising LPDE with the at least one white-rot fungus. In some cases, the concentration of nitrates in the leachate increases to at least about 2 ppm in twelve days following contacting the LPDE or plastic waste comprising LPDE with the at least one white-rot fungus. In some cases, the concentration of nitrates in the leachate increases to at least about 3 ppm in twelve days following contacting the LPDE or plastic waste comprising LPDE with the at least one white-rot fungus. In some cases, the concentration of nitrates in the leachate increases to at least about 4 ppm in twelve days following contacting the LPDE or plastic waste comprising LPDE with the at least one white-rot fungus. In some cases, the concentration of nitrates in the leachate increases to at least about 5 ppm in twelve days following contacting the LPDE or plastic waste comprising LPDE with the at least one white-rot fungus.

In some cases, the concentration of nitrates in the leachate increases in six days following contacting the LPDE or plastic waste comprising LPDE with the at least one white-rot fungus. In some cases, the concentration of nitrates in the leachate increases to at least about 0.5 ppm in six days following contacting the LPDE or plastic waste comprising LPDE with the at least one white-rot fungus. In some cases, the concentration of nitrates in the leachate increases to at least about 1 ppm in six days following contacting the LPDE or plastic waste comprising LPDE with the at least one white-rot fungus. In some cases, the concentration of nitrates in the leachate increases to at least about 2 ppm in six days following contacting the LPDE or plastic waste comprising LPDE with the at least one white-rot fungus. In some cases, the concentration of nitrates in the leachate increases to at least about 3 ppm in six days following contacting the LPDE or plastic waste comprising LPDE with the at least one white-rot fungus. In some cases, the concentration of nitrates in the leachate increases to at least about 4 ppm in six days following contacting the LPDE or plastic waste comprising LPDE with the at least one white-rot fungus. In some cases, the concentration of nitrates in the leachate increases to at least about 5 ppm in six days following contacting the LPDE or plastic waste comprising LPDE with the at least one white-rot fungus.

EXAMPLES

Example 1

Identifying the Combination for Complete LDPE Degradation

Eight groups were tested with different combinations of variables to identify those combinations that achieve complete LDPE degradation (Table 1). The variables included *Phanerochaete chrysosporium* (P.C.), LDPE (3 mg), heating LDPE at 120° C. for 4 minutes, etching LDPE with 3% citric acid for 10 minutes, and adding a synthetic leachate (Table 2).

Synthetic leachate-infused-potato-dextrose agar (PDA) was prepared by boiling and setting overnight. The pH of the agar-infused synthetic leachate was 4.5. 3 mg LDPE with an approximate surface area of 115 $mm^2$ was used to test each group. For groups where the LDPE was heated, heating was done at 120° C. for 4 minutes. For groups where LDPE was etched, etching was performed using 3% citric acid for 10 minutes, followed by thoroughly rinsing and drying. The weight of LDPE after the pretreatment method of heating or etching remained 3 mg.

Each group contained 10 samples. All 80 samples were inoculated with *Phanerochaete chrysosporium* by placing the LDPE was into the culture containing the fungus at an optical density of 2.5 in a 10 microliter inoculation solution. The experiments were conducted at room temperature.

TABLE 1

Details of sample preparation for each group

| | Group Composition | | | | |
|---|---|---|---|---|---|
| Group Number | P.C. | S. Leachate | Etching LDPE | Heating LDPE | LDPE |
| 1 | Y | | | | Y |
| 2 | Y | | | Y | Y |
| 3 | Y | | Y | | Y |
| 4 | Y | | Y | Y | Y |
| 5 | Y | Y | | | Y |
| 6 | Y | Y | | Y | Y |

TABLE 1-continued

Details of sample preparation for each group

| Group Number | Group Composition | | | | |
|---|---|---|---|---|---|
| | P.C. | S. Leachate | Etching LDPE | Heating LDPE | LDPE |
| 7 | Y | Y | Y | | Y |
| 8 | Y | Y | Y | Y | Y |

TABLE 2

Synthetic leachate composition

| Chemical components | Amount per liter |
|---|---|
| $MgSO_4$ | 156 mg |
| $CaCl_2$ | 2882 mg |
| PO | 324 mg |
| $CaCO_3$ | 3012 mg |
| $NH_4$ | 2400 mg |
| NaCl | 1440 mg |
| $MnSO_4$ | 330 mg |
| Distilled water | 1 liter |

Microscopic images were taken to track degradation on a daily basis at a 4× magnification. Weights were measured using a JF2004 electronic balance. However, weight could not be measured in samples for Group 8 at the end of 6-day period due to either no remaining visible LDPE or only one or two pieces that were too small to measure (with surface area of approximately 0.5-1 mm$^2$). Photographs of samples were taken at 6-day intervals. ImageJ was used to measure surface area and optical density. $CO_2$ production was measured using a homemade pneumatic trough. Electro-spray Ionization Mass spectroscopy (ESI-MS) was used to measure the relative charge of chemical compounds. Ammonia, nitrate, and nitrite were measured using a Carolina Water Quality Monitoring Kit. Stat Plus and Microsoft Excel were used for statistical analysis.

Measurements for all groups were made every 6 days for a 12-day period. The measurements made included weight, surface area, and $CO_2$ production for LDPE degradation. Additionally, leachate remediation was measured using optical density and measuring ammonia, nitrate, and nitrite levels after 12 days. ESI-MS measurements were made for samples of agar, P.C.+synthetic leachate, and Group 8 (at Day 5 and Day 12).

Figure 2:
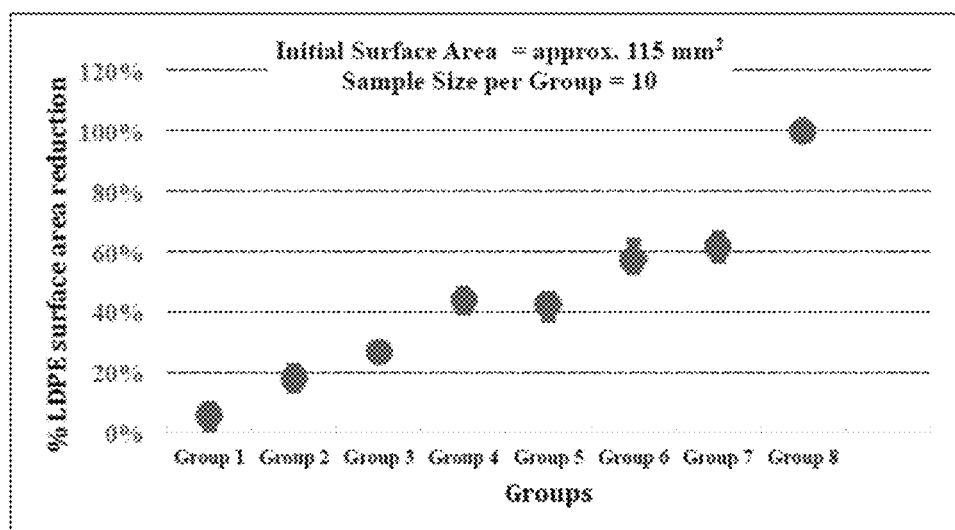
FIG. 2: Percentage of LDPE surface area reduction measured using ImageJ after 6 days.

Group 8 achieved near 100% LDPE decomposition (FIG. 1). The LDPE appeared to be cleaved from the outside to the inside. There was either no visibly remaining pieces of LDPE or only one or two small pieces of LDPE on day 6 in Group 8. In this group, the surface area of LDPE dropped from 115 mm$^2$ to 0.5-0.2 mm$^2$, while the percentage of degradation was 99.6-99.9% (FIG. 2).

Figure 3:
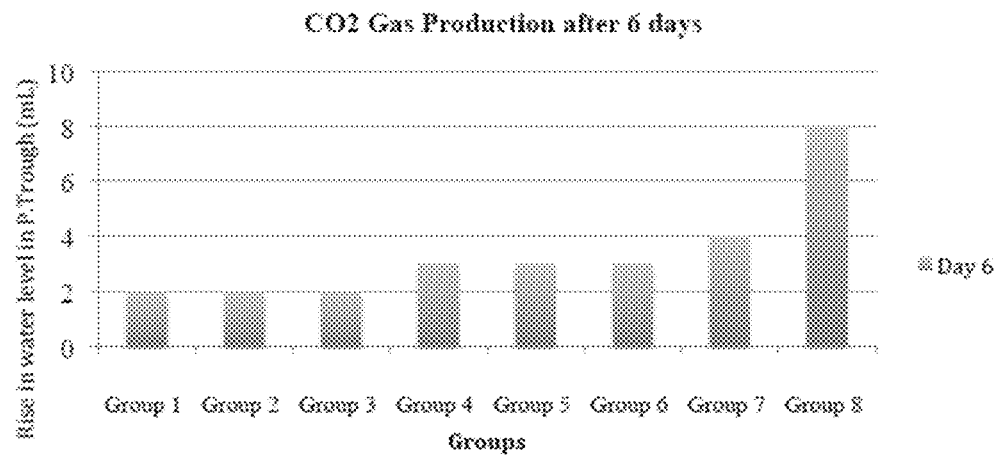
FIG. 3: $CO_2$ gas production measured using a pneumatic trough after 6 days.

LDPE is made up of repeating —$CH_2CH_2$— units. *Phanerochaete chrysosporium* is believed to cleave the LDPE units starting from the surface of the material. Since this entire process is believed to be aerobic, the most oxidized form of carbon, carbon dioxide ($CO_2$), is produced. The $CO_2$ produced is shown in FIG. 3, which shows a plot of change in water levels using a pneumatic trough (Y-axis) for each group. Groups 1-4, which contained no leachate, had a rise in water level of 2-3 mL, likely due to $CO_2$ production resulting from fungal respiration and a slight LDPE degradation (as observed by data from surface area reduction). Groups 5-7, which contained leachate, exhibited a rise in water level of 3-4 mL, due to leachate remediation. Group 8 had the highest rise in water level, which was 8 mL, due to the highest LDPE degradation.

Figure 4:
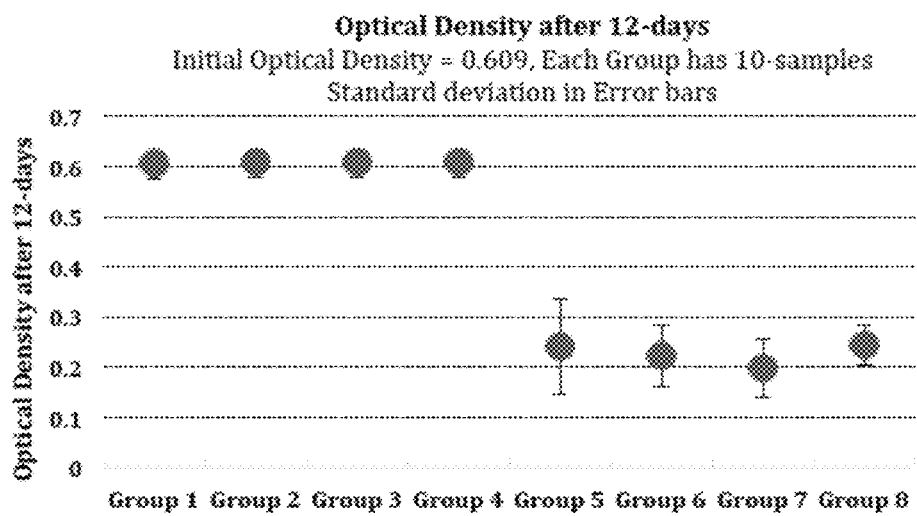
FIG. 4: Optical density measurements using ImageJ after 12 days.

Although a minimal change in optical density was observed in Groups 1-4 (likely due to agar), a decrease in optical density was observed in all samples of Groups 5-8, indicating leachate remediation (FIG. 4). The optical density in these groups dropped from 0.6 to 0.3-0.1. High levels of ammonia also dropped to trace levels after 12 days. The nitrate levels also increased, indicating that the ammonia was converted to nitrate (Table 3).

TABLE 3

Changes in ammonia, nitrate and nitrite concentrations after 12 days

| Days | Ammonia | Nitrate | Nitrite |
|---|---|---|---|
| Day 0 | >8 ppm | 0 ppm | 0 ppm |
| Day 12 | 0.5 ppm | 5.0 ppm | 0 ppm |

Figure 5A:
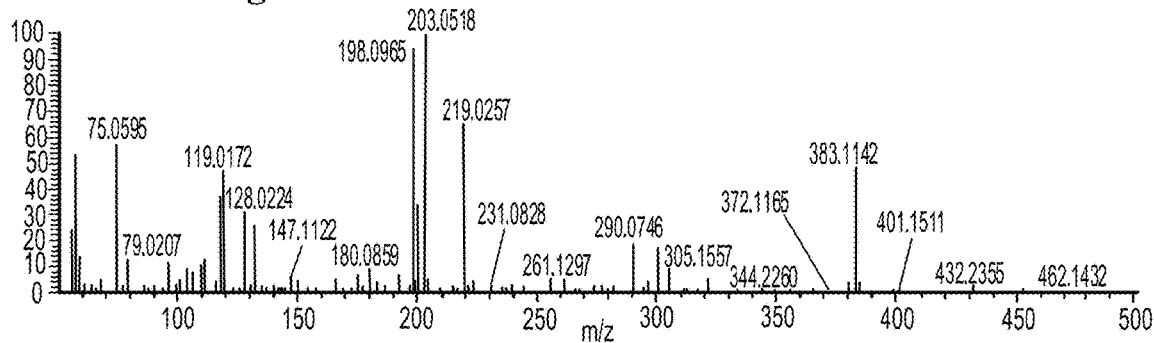
FIGS. 5A-C: ESI-MS measurements from various samples. ESI-MS produced graphs with mass/charge (m/z) (X-axis) versus intensity of charge (Y-axis).
Figure 5B:
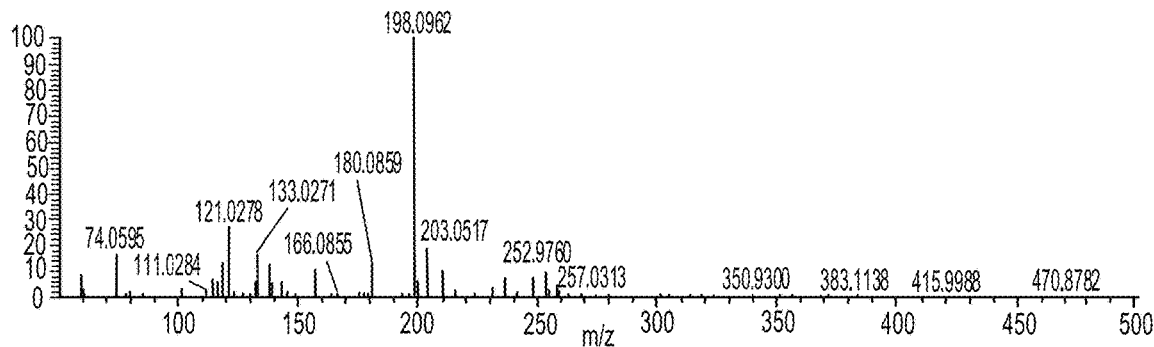
Figure 5C:
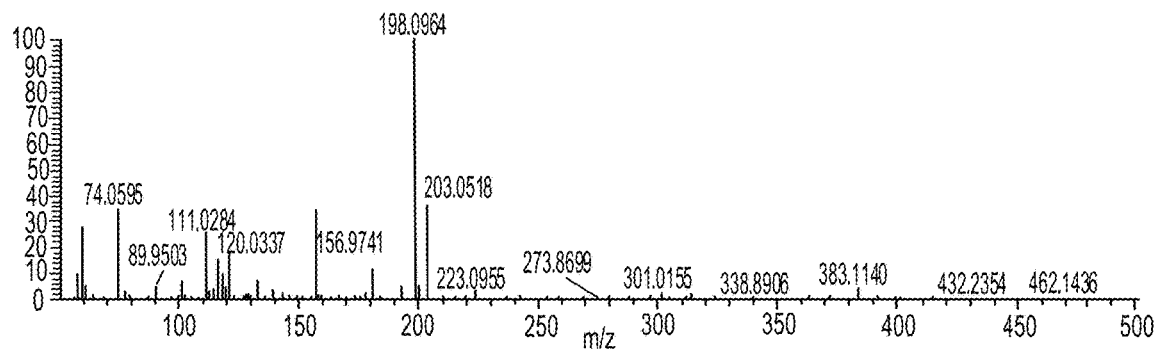

ESI-MS data analysis suggested that *Phanerochaete chrysosporium* was remediating leachate and the LDPE was degraded to trace levels of organics (FIG. 5A-C). Based on the ESI-MS data, carbonate, ammonia, and chloride from synthetic leachate fell to insignificant levels. The byproducts of the entire process are $CO_2$, $H_2O$, nitrates, and trace levels of organics. In summary, the results demonstrate that *Phanerochaete chrysosporium*, while degrading LDPE, is also remediating leachate.

Example 2

Test of Industrial Viability

Two more experiments were conducted to test the industrial viability of Group 8. The first experiment involved introducing synthetic leachate into pinewood sawdust, inoculating with *Phanerochaete chrysosporium* (the fungus was at an optical density of 2.5 in a 10 μL inoculation solution), and placing heated and etched LDPE into the culture. The experiment was conducted at room temperature. The second experiment was the same as the first experiment except that instead of 3 mg LDPE, 900 mg LDPE was placed into the culture.

Figure 6:
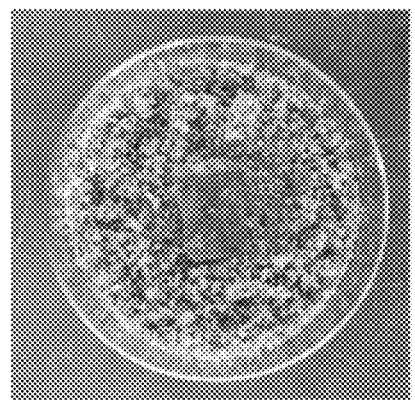
FIG. 6: Photographs showing degradation of LDPE on bioavailable medium (e.g., pinewood sawdust) instead of agar after 6 days.
Figure 6:
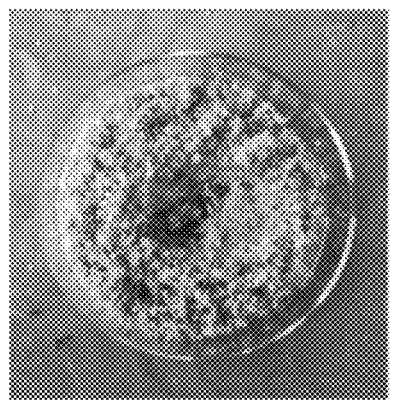
Figure 7:
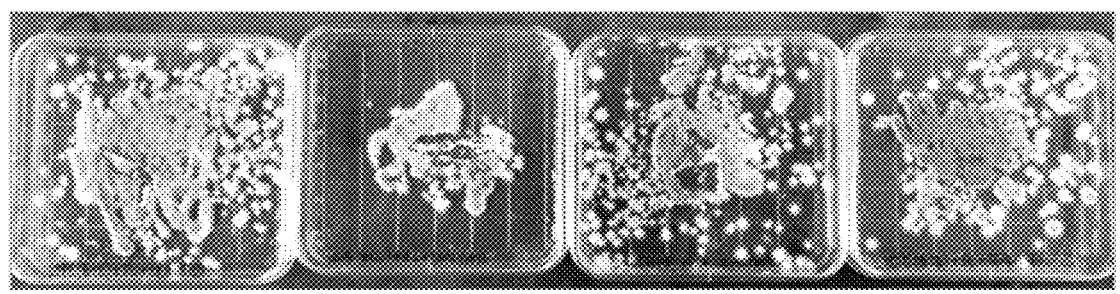
FIG. 7: Photographs showing degradation of 900 mg LDPE on bioavailable medium (e.g., pinewood sawdust) instead of agar at Day 3 and Day 6.
Figure 7:
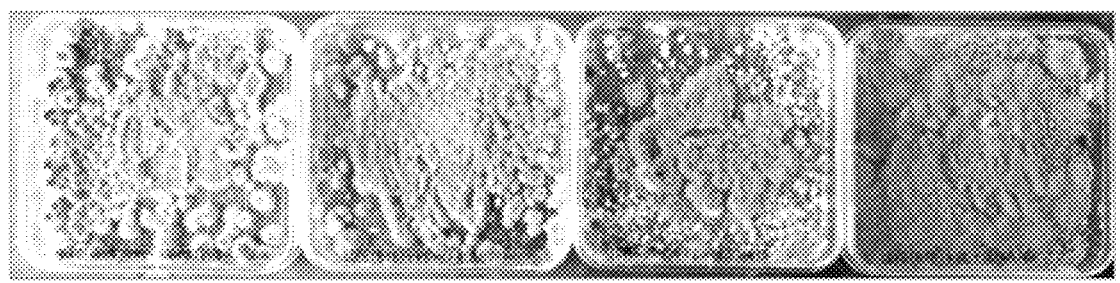

The results suggest that LDPE, after being heated and etched, can be degraded nearly 100% by *Phanerochaete chrysosporium* in pinewood sawdust (FIG. 6). The larger LDPE pieces (900 mg) were also completely degraded (FIG. 7).

Collectively, the results provided herein demonstrate that the methods disclosed have important implications for landfill and ocean health, which can be implemented feasibly using activated sludge infrastructure of existing landfills. The methods disclosed herein could be used on-site, at landfills, at a low cost.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for degrading Low Density Polyethylene (LDPE), the method comprising:
   heating plastic waste comprising LDPE at a temperature of about 90° C. to about 150° C.;
   and contacting the plastic waste with a composition comprising at least one white-rot fungus.

2. The method of claim 1, wherein the white-rot fungus is selected from a group consisting of *Phanerochaete* fungus, *Phlebia* fungus, *Trametes* fungus, *Pleurotus* fungus, *Bjerkandera* fungus, and mixtures thereof.

3. The method of claim 2, wherein the white-rot fungus is selected from a group consisting of *Phanerochaete chrysosporium, Phanerochaete sordida, Pleurotus ostreatus, Pleurotus* ostreatus var. columbines, *Lentinula edodes, Ganoderma lucidum, rametes versicolor, Bjerkandera adjusta, Trametes versicolor, Pleurotus* ostreatus, and mixtures thereof.

4. The method of claim 1, wherein the white-rot fungus is not naturally found on the LDPE or in the plastic waste comprising the LDPE prior to the contacting.

5. The method of claim 1, wherein the contacting comprises inoculating.

6. The method of claim 1, wherein the plastic waste is contacted with an amount of at least one white-rot fungus to colonize the plastic with the at least one white-rot fungus.

7. The method of claim 1, wherein the plastic waste is heated for at least 2 minutes.

8. The method of claim 1, the method further comprising etching the plastic waste before contacting with the white-rot fungus.

9. The method of claim 8, wherein the plastic waste is etched with a weak acid.

10. The method of claim 8, wherein the plastic waste is etched for at least 8 minutes.

11. The method of claim 9, wherein the weak acid is selected from a group consisting of lactic acid, citric acid, malic acid, oxalic acid, acetic acid, tartaric acid, adipic acid, succinic acid, maleic acid, glutamic acid, fumaric acid, pyruvic acid, gluconic acid, picric acid, aspartic acid, and terebic acid.

12. The method of claim 1, wherein the method further comprises adding a medium with a high C/N ratio to the plastic waste.

13. The method of claim 12, wherein the medium comprises leachate.

14. The method of claim 12, wherein the pH of the medium is at about pH 3.5 to about pH 5.

15. The method of claim 1, wherein after heating, the temperature of the plastic waste is maintained at about 25° C. to about 60° C.

16. The method of claim 1, wherein the method further comprises adding agar, compost, organic waste, wood waste, woodchips or sawdust to the plastic waste.

17. The method of claim 1, wherein at least 50% of the LDPE by weight is degraded in six days following contacting the plastic waste with the at least one white-rot fungus.

18. The method of claim 1, wherein the optical density of the leachate decreases at least 50% in twelve days following contacting the plastic waste with the at least one white-rot fungus.

19. The method of claim 1, wherein the concentration of ammonia in the leachate decreases in twelve days following contacting the plastic waste with the at least one white-rot fungus.

20. The method of claim 1, wherein the concentration of nitrates in the leachate increases in twelve days following contacting the plastic waste with the at least one white-rot fungus.

* * * * *

UNITED STATES PATENT AND TRADEMARK OFFICE
CERTIFICATE OF CORRECTION

PATENT NO. : 11,583,904 B2
APPLICATION NO. : 16/849026
DATED : February 21, 2023
INVENTOR(S) : Shloka Janapaty Page 1 of 1

It is certified that error appears in the above-identified patent and that said Letters Patent is hereby corrected as shown below:

In the Claims

In Column 13, Lines 16-17, in Claim 3, delete "rametes versicolor, Bjerkandera adjusta, Trametes versicolor," and insert -- Trametes versicolor, Bjerkandera adusta, --, therefor.

Signed and Sealed this
Fourth Day of April, 2023

Katherine Kelly Vidal
*Director of the United States Patent and Trademark Office*